(12) United States Patent
Sanchez et al.

(10) Patent No.: US 8,461,405 B2
(45) Date of Patent: Jun. 11, 2013

(54) PROCESS FOR THE PRODUCTION OF BRANCHED ALKYLBENZENES THAT USES A RENEWABLE CARBON SOURCE

(75) Inventors: Eric Sanchez, Saint Genis Laval (FR); Emmanuelle Guillon, Vourles (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 236 days.

(21) Appl. No.: 13/100,887

(22) Filed: May 4, 2011

(65) Prior Publication Data
US 2011/0275871 A1 Nov. 10, 2011

(30) Foreign Application Priority Data

May 6, 2010 (FR) .................................. 10 01950

(51) Int. Cl.
*C07C 2/66* (2006.01)
*C07C 2/12* (2006.01)
*C07C 2/24* (2006.01)

(52) U.S. Cl.
USPC ........... 585/323; 585/455; 585/531; 585/517; 585/533

(58) Field of Classification Search
USPC .......................... 585/323, 455, 531, 517, 533
See application file for complete search history.

(56) References Cited

U.S. PATENT DOCUMENTS

| 4,959,491 A | 9/1990 | Threlkel |
| 2004/0254411 A1 | 12/2004 | Steinbrenner et al. |

FOREIGN PATENT DOCUMENTS

| WO | 8807030 A2 | 9/1988 |
| WO | 2010015732 A1 | 2/2010 |

OTHER PUBLICATIONS

Philips C.B., et al., "Production of Ethylene from Hydrous Ethanol on H-ZSM-5 under Mild Conditions," Industrial and Engineering Chemical Research, Nov. 3, 1997, vol. 36, pp. 4466-4475; Cited in Search Report, dated Oct. 21, 2010, issued in corresponding FR 1001950.
Search Report, dated Oct. 21, 2010, issued in corresponding FR 1001950.

*Primary Examiner* — Thuan D Dang
(74) *Attorney, Agent, or Firm* — Millen, White, Zelano & Branigan, P.C.

(57) ABSTRACT

A process for the production of alkylbenzenes in the presence of an aromatic feedstock and an olefinic stream produced from an ethanol feedstock, itself produced from a renewable source obtained from biomass, is described, with said process comprising at least:
a) A stage for purification of said ethanol feedstock,
b) A stage for dehydration of said purified ethanol feedstock, obtained from said stage a), into an effluent that is for the most part ethylene,
c) At least one stage for separation of the water that is present in said effluent that is for the most part ethylene obtained from said stage b),
d) A first stage for oligomerization of said effluent that is for the most part ethylene in the presence of at least one catalyst that comprises at least one element of group VIII,
e) A second stage for oligomerization of at least some of the effluent that is obtained from said stage d) in the presence of at least one amorphous catalyst or at least one zeolitic catalyst,
f) A stage for fractionation of the effluent that is obtained from said oligomerization stage e) in such a way as to recover at least one olefin-enriched olefinic stream that has a number of carbon atoms that is greater than or equal to 9,
g) An alkylation stage of said olefinic stream that is obtained from said stage f) by at least one aromatic feedstock.

15 Claims, 1 Drawing Sheet

PROCESS FOR THE PRODUCTION OF BRANCHED ALKYLBENZENES THAT USES A RENEWABLE CARBON SOURCE

TECHNICAL FIELD

This invention relates to the field of the production of aromatic compounds that belong to the families of alkylbenzenes by a non-conventional method that uses a renewable carbon source as an olefinic feedstock for the implementation of an alkylation stage. The alkylbenzenes that are obtained according to the process of the invention constitute precursors of choice for the formulation of detergents and in particular biodegradable detergents, for example by sulfonation.

PRIOR ART

The alkylbenzenes are generally produced by alkylation of aromatic compounds, preferably by alkylation of benzene, by means of olefin(s) having 9 to 16, preferably 10 to 14, carbon atoms per molecule. The conventional processes of the production of alkylbenzenes use olefins that are obtained from petroleum fractions that have undergone several treatments before being able to be used as an olefinic reagent for the alkylation reaction in the presence of benzene. In particular, the conventional processes for the production of alkylbenzenes most often comprise the concatenation of the following stages:
 1—The separation of normal paraffins that are present in a C9-C16 fraction,
 2—The dehydrogenation of normal paraffins into C9-C16 olefins,
 3—The selective hydrogenation of the diolefins that are produced during said dehydrogenation stage 2),
 4—The optional elimination of the aromatic compounds that are produced during said stage 2) by any means that is known to one skilled in the art (separation, adsorption, . . . ),
 5—The alkylation of benzene by the C9-C16 olefins so as to produce alkylbenzenes in the presence of an acid catalyst in solid form (silica-alumina, zeolites, clays) or in liquid form (HF).

Such a process for the production of alkylbenzenes has already been widely described, for example in the patents U.S. Pat. Nos. 5,245,094, 5,276,231 and 5,334,793 as well as in Ullmann's Encyclopedia, $5^{th}$ Volume A 25, page 766.

So as to limit the formation of undesirable compounds, in particular those of aromatic compounds, said conventional processes for the production of alkylbenzenes, starting from a paraffinic fraction as an olefin source for the alkylation reaction, operate under conditions such that the conversion of the paraffins into olefins remains low: the conversion of normal paraffins into olefins, per pass, is generally estimated to be between 5 and 30% over the dehydrogenation stage (stage 2 indicated above). This low conversion constitutes a major drawback of this type of process to the extent that the desired olefins are produced in a small quantity and that the normal paraffins, not converted into said dehydrogenation stage, are present, in a large proportion, in the feedstocks that are introduced into the reactors that implement the stages for selective hydrogenation (stage 3 above), elimination of aromatic compounds (stage 4 above), and alkylation (stage 5 above). The low conversion of normal paraffins into olefins therefore constitutes a major drawback as soon as said stages 3, 4, and 5 undergo the presence of such paraffins without being able to be transformed, creating a significant dimensioning of the process and inevitably bringing about major consequences in terms of investment and operating costs. In addition, the presence of a large quantity of paraffins in the reactor that produces the alkylation stage is detrimental to the alkylation catalyst that then deactivates quickly.

Furthermore, the advantage of producing modified alkylbenzenes (MAB), whose alkyl chain is branched (WO 99/05082, U.S. Pat. No. 6,525,233) for the purpose of an improvement in the solubility of linear alkylbenzene sulfonates (LAS for linear alkylbenzene sulfonates) at low temperature, an improvement in their sensitivity to the hardness of water, and an improvement in their detergent properties, was taught. However, the conventional processes for the production of alkylbenzenes lead to the production of linear alkylbenzenes (LAB) whose alkyl chain is lacking in any branching. Also, to meet the demand for modified alkylbenzenes, processes were considered that integrate an additional stage for isomerization of the paraffins placed either upstream from the process (WO 01/05733, U.S. Pat. No. 6,187,981) or between the selective hydrogenation stage and the alkylation stage (U.S. Pat. No. 6,670,516). The introduction of an isomerization stage adds to the complexity of the concatenation of the processes for the production of alkylbenzenes, which then comprise at least 6 stages.

In such a way as to remedy the drawbacks encountered by the implementation of the conventional processes for the production of alkylbenzenes, this invention proposes providing a new process for the production of alkylbenzenes of which one of the intermediate stages, prior to the implementation of the alkylation stage, leads to the production of an effluent that is composed for the most part of branched olefins, thus avoiding not only the implementation of an isomerization stage but also the undesirable presence of paraffins in the alkylation reactor; this accounts for an improved stability of the alkylation catalyst, in particular when the latter is an acidic solid catalyst, for example a zeolitic catalyst. The process according to the invention uses a renewable carbon source in the form of bioethanol as an olefin source and does not produce intermediate effluents that contain undesirable compounds, such as paraffins or aromatic compounds in the prior processes, for the concatenation of the different stages: the dimensioning of the process according to the invention is thus better adjusted to the strict requirement for production of alkylbenzenes without the necessity of using large capacities, in particular at the level of the dimensioning of different reactors, for incorporating unconverted and/or undesirable compounds. The process according to the invention, while avoiding the necessity for initiating the recycling of paraffinic streams and the elimination of aromatic compounds, makes it possible to produce, with investment and operating costs that are considerably reduced relative to those of the prior art, a quality of desired alkylbenzenes for then being updated in the formulation of biodegradable detergents.

DESCRIPTION OF THE INVENTION

This invention has as its object a process for the production of at least one aromatic compound that belongs to the family of alkylbenzenes in the presence of at least one aromatic feedstock that comprises at least one compound that has a benzene core and at least one olefinic stream that is produced from an ethanol feedstock, itself produced from a renewable source that is obtained from biomass, whereby said process comprises at least:
 a) A stage for purification of said ethanol feedstock,
 b) A stage for dehydration of said purified ethanol feedstock, obtained from said stage a), into an effluent that is for the most part ethylene, comprising water, whereby said stage operates in the presence of at least one amorphous acid catalyst or at least one zeolitic acid catalyst, c) At least one stage for separation of the water that is present in said effluent that is for the most part ethylene obtained from said stage b), d) A first stage for oligomerization of said effluent that is for the most part ethylene, obtained from said stage c), in the presence of at least one catalyst that comprises at least one element of group VIII for producing at least one light olefinic effluent that comprises at least 50% by weight, relative to the total mass of the olefins that are contained in said light olefinic effluent, of olefins that have a number of carbon atoms that is greater than or equal to 4, e) A second stage for oligomerization of at least some of the effluent that is obtained from said stage d) in the presence of at least one amorphous catalyst or at least one zeolitic catalyst for producing at least one olefinic effluent that comprises at least 50% by weight, relative to the total mass of the olefins that are contained in said olefinic effluent, of olefins that have a number of carbon atoms that is greater than or equal to 8, f) At least one stage for fractionation of the effluent that is obtained from said oligomerization stage e) in such a way as to recover at least one olefin-enriched olefinic stream that has a number of carbon atoms that is greater than or equal to 9, g) An alkylation stage of said olefinic stream that is obtained from said stage f) by at least one aromatic feedstock that comprises at least one compound that has a benzene core.

In accordance with the process according to the invention, the olefinic stream that is used for the implementation of the alkylation reaction according to said stage g) of the process of the invention comes from an ethanol feedstock, which was subjected to a series of treatments, in particular to the treatments implemented in stages a) to f) of the process according to the invention. Said ethanol feedstock, used in the process of the invention, is produced from a renewable source that is obtained from biomass and will consequently be called "bioethanol feedstock" throughout the rest of the description.

Said bioethanol feedstock is a feedstock that is produced biologically, more specifically by fermentation of sugars obtained from, for example, sugar-producing crops of the sugarcane type (saccharose, glucose, fructose, sucrose), beet scraps, or else obtained from amylased plants (starch) or lignocellulosic biomass or hydrolyzed cellulose (glucose for the most part, and xylose, galactose), containing variable quantities of water. Said bioethanol feedstock is advantageously produced by fermentation from three sources: 1) sucrose from cane sugar or beet scraps, 2) starch that is present in grains and tubers, and 3) cellulose and hemicellulose that are present in wood, herbs and other lignocellulosic biomasses, with starch, cellulose and hemicellulose being hydrogenated in advance before undergoing the fermentation stage.

The bioethanol feedstock that is used in the process according to the invention contains for the most part ethanol, i.e., it has an ethanol content by weight of at least 50% by weight, and preferably at least 70% by weight. It advantageously also has a water content that is greater than 2% by weight, preferably greater than 5% by weight, and in a preferred manner greater than 10% by weight. Said bioethanol feedstock has, moreover, a content of cationic impurity, such as, for example, the ions $Na^+$, $Ca^{2+}$, $Mn^{2+}$, $Fe^{2+}$, $Cu^{2+}$, $Zn^{2+}$, advantageously less than 0.5% by weight, a content of anionic impurity, such as, for example, the ions of $Cl^-$, sulfate, nitrite, nitrate, phosphates, advantageously less than 0.5% by weight, a content of alcohol, other than ethanol, such as, for example, methanol or butanol, advantageously less than 10% by weight, and preferably less than 5% by weight, a content of oxidized compounds other than the alcohols, such as, for example, ethers, acids, ketones, aldehydes, and/or esters that is advantageously less than 1% by weight, and a content of nitrogen and sulfur that is advantageously less than 0.5% by weight, whereby the percentages by weight are expressed relative to the total mass of said bioethanol feedstock.

In accordance with stage a) of the process according to the invention, the bioethanol feedstock undergoes a purification stage in such a way as to eliminate the cationic and anionic impurities as well as at least one part of the oxidized compounds that are present in said bioethanol feedstock for limiting the deactivation of the dehydration catalyst that is placed downstream.

Said purification stage is advantageously implemented by means that are known to one skilled in the art, such as, for example, the use of at least one resin, the adsorption of impurities and oxidized compounds in a solid that is selected from among the molecular sieves, active carbon, alumina and zeolites, and distillation (for producing in particular a purified fraction of ethanol and a fraction that comprises the organic impurities) so as to obtain a purified feedstock that corresponds to the level of impurities compatible with the dehydration catalyst. One pretreatment stage is advantageously implemented by hydrogenation of the unsaturated oxidized compounds in the presence of a nickel-based catalyst, whereby said pretreatment stage is carried out before or after said purification stage, preferably after.

In accordance with stage b) of the process according to the invention, the purified bioethanol feedstock, obtained from said stage a), undergoes a stage for dehydration into an effluent that is for the most part ethylene and that comprises water, whereby said stage operates in the presence of at least one dehydration catalyst that is known to one skilled in the art, in particular an acid catalyst that can be either amorphous or zeolitic.

In the case where the catalyst that is used in said dehydration stage b) is a zeolitic acid catalyst, said catalyst comprises at least one zeolite that is selected from among the zeolites that have at least openings of pores containing 10 or 12 oxygen atoms (10 MR or 12 MR). It is actually known to define the size of pores of the zeolites by the number of oxygen atoms that form the annular cross-section of the channels of zeolites, called "member rings" or MR in English. In a preferred manner, said zeolitic catalyst comprises at least one zeolite that has a structural type that is selected from among the following structural types: MFI, FAU, MOR, FER, and BEA. The zeolite that is present in the zeolitic catalyst that is used for the implementation of said stage b) of the process according to the invention is advantageously modified by dealuminification or desilification according to any method of dealuminification or desilification that is known to one skilled in the art.

In the case where the catalyst that is used in said dehydration stage b) is an amorphous acid catalyst, said catalyst comprises at least one porous refractory oxide that is selected from among alumina, alumina activated by a deposit of mineral acid, and silica-alumina.

Said amorphous or zeolitic dehydration catalyst, used in said stage b) of the process according to the invention, advantageously also comprises at least one oxide-type matrix, also called a binder. Said matrix is amorphous or poorly crystallized. It is advantageously selected from among the elements of the group that is formed by clays (for example, from among the natural clays such as kaolin or bentonite), magnesia, aluminas, silicas, silica-aluminas, aluminates, titanium oxide, boron oxide, zirconia, aluminum phosphates, titanium phosphates, zirconium phosphates and carbon. Preferably, said matrix is selected from among the elements of the group that is formed by aluminas, silicas and clays. In an advantageous manner, said binder has a macroporous texture as described in the patent application US2009/088595.

The dehydration catalyst that is used in said stage b) of the process according to the invention is advantageously formed into seeds of different shapes and sizes. It is advantageously used in the form of cylindrical or multilobar extrudates such as bilobar, trilobar or polylobar extrudates of straight or twisted shape, but it can optionally be manufactured and used in the form of crushed powder, tablets, rings, balls, wheels, or spheres. Said dehydration catalyst preferably comes in the form of extrudates or balls.

Said dehydration stage b) of the process according to the invention advantageously operates at a temperature of between 250 and 600° C., preferably between 300 and 600° C., and in a preferred manner between 300 and 500° C., at an absolute pressure of between 0.1 and 5 MPa, preferably between 0.1 and 2.5 MPa, and in a preferred manner between 0.1 and 1 MPa, and at an hourly speed by weight (mass rate of the feedstock per gram of catalyst) of between 0.1 and 50 h$^{-1}$, and preferably between 0.5 and 15 h$^{-1}$.

Said dehydration stage b) is implemented under conditions such that as a function of the selection of the dehydration catalyst and operating conditions, the ethylene production is maximized. The dehydration reaction that is implemented in stage b) of the process according to the invention is as follows:

$$2C_2H_5OH \rightarrow 2CH_2=CH_2+2H_2O$$

Said stage b) produces an effluent that is for the most part ethylene, i.e., an effluent that comprises at least 95% by weight, preferably at least 97% by weight, and in a more preferred manner at least 98% by weight of ethylene relative to the total mass of the carbon compounds that are formed and present in said effluent that is produced in said stage b). Said effluent can also comprise other hydrocarbon-containing, hydroxycarbon-containing or oxycarbon-containing compounds in a very minority proportion; in particular, said effluent also advantageously comprises less than 5% by weight, preferably less than 3% by weight, and in a preferred manner less than 2% by weight of compounds that have a number of carbon atoms that is greater than or equal to 3, and oxidized compounds such as, for example, $CO_2$, CO, diethyl ether or acetaldehyde, whereby the percentages are expressed in terms of percentages by weight relative to the total mass of the carbon compounds that are formed and present in said effluent that is produced in said stage b). Said effluent that is for the most part ethylene advantageously comprises 25 to 40% by weight of water.

The conversion of the bioethanol feedstock in the dehydration stage b) is advantageously greater than 90%, preferably greater than 95%, and in a more preferred manner greater than 98%. The conversion of the bioethanol feedstock is defined as the ratio of the difference between the mass rate of the bioethanol feedstock ($C_2H_5OH$) at the input and the mass rate of the bioethanol feedstock ($C_2H_5OH$) at the output of stage b) to the mass rate of the bioethanol feedstock at the input of said stage b).

A water-based diluent that comes from a feedstock outside of the process according to the invention is advantageously added to the purified bioethanol feedstock according to said stage a), before the implementation of said stage b), whereby the molar ratio of diluent to purified feedstock is advantageously between 0.5 and 20. The dilution of said purified feedstock makes it possible to stabilize the dehydration catalyst that is used in said stage b) of the process according to the invention.

In accordance with the process of the invention, said dehydration stage b) is advantageously implemented in at least one reactor that operates in a fixed bed, for example in a manner that is analogous to the one described in the patent U.S. Pat. No. 4,396,789, in a moving bed or in a fluidized bed.

In the case where stage b) is implemented in a fluidized bed, the dehydration catalyst comes in the form of balls, with a diameter that is advantageously less than 500 microns and preferably less than 300 microns. In the case where stage b) is implemented in a moving bed, the dehydration catalyst comes in the form of balls with a diameter that is advantageously between 0.5 and 3 mm. In the case where stage b) is implemented in a fixed bed, the dehydration catalyst comes in the form of balls with a diameter that is advantageously between 0.5 and 3 mm or in the form of extrudates with a diameter that is advantageously between 0.5 and 3 mm and with a length that is advantageously between 1.5 and 6 mm.

The dehydration of said ethanol feedstock is generally accompanied by a deactivation of the dehydration catalyst by coking and/or adsorption of inhibiting compounds. Said dehydration catalyst is advantageously regenerated. In the case where stage b) is implemented in a fixed bed, the regeneration of the dehydration catalyst that is used in said stage b) is advantageously performed under a stream of air, for example by using recirculation of the combustion air, with or without water, so as to dilute the oxygen and control the regeneration exothermy. In this case, it is advantageously possible to adjust the oxygen content at the input of the reactor by an addition of air. The regeneration is carried out at a pressure of between atmospheric pressure (0 bar, relative) and the reaction pressure. The regeneration temperature is advantageously selected between 400 and 600° C.; it can advantageously vary during regeneration. The end of the regeneration is detected when the consumption of oxygen is zero.

In the case where stage b) is implemented in a moving or fluidized bed, for example in a manner that is similar to the one described in the patent U.S. Pat. No. 4,134,926, the regeneration of the catalyst is done continuously.

In accordance with said stage c) of the process according to the invention, the effluent that is obtained from said stage b) undergoes at least one stage for separation of the water that is present in the effluent that is produced during stage b).

Preferably, said separation stage is followed by at least one stage for purification of said effluent that is for the most part ethylene from which water was eliminated in advance. Said stage c) of the process according to the invention makes it possible to eliminate the impurities that are harmful for the oligomerization catalysts that are used for the implementation of stages d) and e), carried out downstream, and in particular said stage c) makes possible the elimination of the oxidized compounds that are present in said effluent, in particular $CO_2$, CO, diethyl ether or acetaldehyde.

Said stage c) of the process of the invention that implements at least one stage for separation of the water and/or at least one stage for purification of said effluent that is for the most part ethylene obtained from said stage b) can advantageously be implemented by any method that is known to one skilled in the art, for example by the successive combination of a treatment in a column for washing with water, and then in a column for adsorption with MDEA (methyl diethylamine) or another amine and in a column for washing with soda.

Drying agents can advantageously be used in such a way as to reduce the water content, present in the effluent used as feedstock for the implementation of the subsequent stages d) and e) for oligomerization, with a content that is compatible with the oligomerization catalysts that are used downstream in said stages d) and e) for oligomerization. The water content that is present in the effluent, obtained from said stage c) and sent into said first stage d) for oligomerization of the process of the invention, is advantageously between 0 and 1,000 ppm and preferably between 0 and 500 ppm.

At least one part of the water that is eliminated during said stage c) is advantageously recycled upstream from stage b) for dehydration, the thus recycled water being used as diluent for the purified bioethanol feedstock.

In accordance with the process of the invention, the effluent that is for the most part ethylene obtained from said stage c) is then subjected to a first oligomerization stage d) that is implemented in the presence of at least one catalyst that comprises at least one element of group VIII for producing at least one light olefinic effluent that comprises at least 50% by weight, relative to the total mass of the olefins that are contained in said light olefinic effluent, of olefins that have a number of carbon atoms that is greater than or equal to 4. At least some, i.e., at least 50% by weight, preferably at least 90% by weight, of said effluent that is obtained from said stage c), and very preferably all of said effluent that is obtained from said stage c), is subjected to said first oligomerization stage d).

Preferably, the feedstock that enters the reactor(s) implementing said first oligomerization stage is introduced there mixed with some, and preferably all, of a light olefinic, hydrocarbon-containing effluent that has a number of carbon atoms for the most part between 2 and 4 (C2-C4 light olefinic effluent), which is obtained from an optional separation stage that is described below and preferably implemented between said oligomerization stages d) and e) according to the process of the invention. At least some of the light effluent that comprises the C2 to C4 olefinic compounds obtained from said fractionation stage f) described later in this description is also advantageously recycled to said first oligomerization stage d) of the process according to the invention.

Said first oligomerization stage d) leads to the production of a light olefinic effluent that comprises at least 50% by weight, relative to the total mass of the olefins contained in said light olefinic effluent, of olefins that have a number of carbon atoms that is greater than or equal to 4. In particular, said effluent is rich in olefinic hydrocarbons having a number of carbon atoms of between 4 and 8 and also comprises olefinic hydrocarbons having at least 9 carbon atoms (C9+). More particularly, said light olefinic effluent comprises at least 60% by weight, preferably at least 65% by weight, and in a more preferred manner at least 75% by weight, relative to the total mass of the olefins contained in said light olefinic effluent, of olefins that have a number of carbon atoms that is greater than or equal to 4. Among the olefins that have a number of carbon atoms that is greater than or equal to 4 that are present in said light olefinic effluent, obtained from said stage d), the C4-C8 olefins are in the majority relative to the C9+ olefins, i.e., they represent at least 50% by weight, preferably at least 70% by weight, of the olefins that have at least 4 carbon atoms. In addition to the majority presence of olefins that have a number of carbon atoms that is greater than or equal to 4, said light olefinic effluent also advantageously comprises less than 50% by weight, preferably less than 40% by weight, in a more preferred manner less than 35% by weight, and in an even more preferred manner less than 25% by weight, relative to the total mass of olefins that are contained in said light olefinic effluent, C2 and C3 olefinic compounds, in particular ethylene that has not reacted during the first oligomerization stage d).

The catalyst that is used for the implementation of said first oligomerization stage d) comprises at least one element of group VIII. Said first oligomerization stage is implemented either by homogeneous catalysis, i.e., in the presence of a soluble catalyst, the reaction medium for forming a liquid phase, or by heterogeneous catalysis, i.e., the catalyst, deposited on a solid substrate, is insoluble in the reaction medium.

In a preferred manner, said first oligomerization stage is implemented by heterogeneous catalysis in the presence of at least one catalyst that comprises at least one element of group VIII and at least one porous oxide refractory substrate. Said element of group VIII is preferably selected from among nickel, cobalt, iron, platinum and palladium, and in a more preferred manner, said element of group VIII is nickel. Said porous oxide refractory substrate is preferably selected from among alumina, silica, silica-aluminas, zirconias, titanium oxide, magnesia, clays taken by themselves or in a mixture, and in a more preferred manner, said substrate is an alumina or a silica-alumina.

Said first oligomerization stage d) of the process according to the invention, implemented by heterogeneous catalysis, advantageously operates at a temperature of between 30 and 400° C., preferably between 50 and 300° C., and in a preferred manner between 50 and 200° C., at a pressure of between 0.5 and 10 MPa, preferably between 1 and 10 MPa, and in a preferred manner between 1 and 8 MPa, and at an hourly speed by weight (mass rate of the feedstock per gram of catalyst) of between 0.1 and 10 $h^{-1}$ and preferably between 0.4 and 5 $h^{-1}$.

Said first oligomerization stage can also be advantageously implemented by homogeneous catalysis in the presence of at least one homogeneous catalyst that contains at least one metal precursor that comprises at least one metal of group VIII that is selected from among nickel and iron. In a preferred manner, the homogeneous catalyst that is used in said first oligomerization stage contains, in addition to at least said metal precursor, at least one activator that is preferably selected from the group that is formed by tris(hydrocarbyl) aluminum, hydrocarbylaluminum halides, preferably chlorinated or brominated hydrocarbylaluminum compounds, and aluminoxanes. The tris(hydrocarbyl)aluminum and the hydrocarbylaluminum halides preferably correspond to the general formula $AlR''_n Y_{3-n}$, in which R" represents a monovalent hydrocarbon radical that contains, for example, up to 12 carbon atoms, such as alkyl, aryl, aralkyl, alkaryl or cycloalkyl; Y represents a halogen atom that is preferably selected from among chlorine and bromine, and very preferably Y is chlorine, whereby n can assume a value of 0 to 3. The tris(hydrocarbyl)aluminum and the hydrocarbylaluminum halides that correspond to the general formula $AlR''_n Y_{3-n}$ are preferably selected from among ethylaluminum sesquichloride (EASC), dichloroethylaluminum (EADC), dichloroisobutylaluminum, chlorodiethylaluminum (DEAC), triethylaluminum (TEA) and trimethylaluminum (TMA). These activators can be used alone or in a mixture. The aluminoxanes are preferably selected from among methylaluminoxane (MAO) or modified methylaluminoxane (MMAO), taken by themselves or in a mixture.

Said homogenous catalyst that is advantageously used in said first oligomerization stage advantageously contains at least one additive that is selected from among the Bronsted acid compounds, the Lewis acids and bases and the electron donor organic compounds that contain at least one oxygen atom or at least one nitrogen atom or at least one phosphorus atom or at least one monofunctional or polyfunctional sulfur atom. By way of example, it is possible to cite amines, imines, carboxylic acids, acetals, ketals, ethers or alcohols.

Said first oligomerization stage d) of the process according to the invention, implemented by homogeneous catalysis, advantageously operates under a total pressure of 0 to 20 MPa, preferably from 1 to 10 MPa, and at a temperature of 20 to 180° C., preferably 40 to 140° C.

In accordance with the process of the invention, the effluent that is obtained from said first oligomerization stage d) is introduced into at least one reactor that carries out the implementation of a second oligomerization stage e), which is carried out in the presence of at least one amorphous catalyst or at least one zeolitic catalyst, preferably in the presence of at least one zeolitic catalyst. For an implementation of said stage e) in the presence of an amorphous catalyst, said amorphous catalyst comprises, preferably consists of, an amorphous mineral material that is selected from among the silica-aluminas and the siliceous aluminas. In a very preferred manner, said amorphous catalyst is a silica-alumina. For an implementation of said stage e) in the presence of a zeolitic catalyst, said zeolitic catalyst comprises at least one zeolite that has at least some pore openings that contain 10 or 12 oxygen atoms (10 MR or 12 MR). In a preferred manner, said zeolitic catalyst comprises at least one 10 MR or 12 MR zeolite that is selected from among the aluminosilicate-type zeolites that have an overall Si/Al atomic ratio that is greater than or equal to 10. In a more preferred manner, said zeolitic catalyst comprises at least one zeolite that is selected from among the zeolites ZSM-5, ZSM-12, NU-86, mordenite, ZSM-22, NU-10, ZBM-30, ZSM-11, ZSM-57, IZM-2, ITQ-6, and IM-5, taken by themselves or in a mixture; preferably from among the zeolites ZSM-5, NU-10 and ZBM-30, taken by themselves or in a mixture; in a very preferred manner, the zeolite is the zeolite ZBM-30; and in an even more preferred manner, the zeolite is the zeolite ZBM-30 that is synthesized in the presence of the triethylenetetramine structuring agent. The zeolite that is present in the zeolitic catalyst that is used for the implementation of said stage e) can advantageously undergo several post-treatments that are known to one skilled in the art, for example a modification by dealuminification or desilification according to any method of dealuminification, outside surface passivation or desilification that is known to one skilled in the art. Said catalyst that is used in said stage e) of the process according to the invention, preferably said zeolitic catalyst, also advantageously comprises at least one oxide-type matrix that is also called a binder. It is an amorphous or poorly crystallized matrix that is selected from among the elements of the group that is formed by the clays (for example, from among the natural clays such as kaolin or bentonite), magnesia, aluminas, silicas, silica-aluminas, aluminates, titanium oxide, boron oxide, zirconia, aluminum phosphates, titanium phosphates, zirconium phosphates, and carbon. Preferably, said matrix is selected from among the elements of the group that is formed by aluminas, clays, and silicas; in a more preferred manner, said matrix is selected from among aluminas; and in an even more preferred manner, said matrix is gamma-alumina. Said catalyst that is used in said second oligomerization stage e) of the process according to the invention is advantageously formed into seeds of different shapes and sizes. It is advantageously used in the form of cylindrical or multilobar extrudates such as bilobar, trilobar, or multilobar extrudates of straight or twisted shape, but it can optionally be manufactured and used in the form of crushed powder, tablets, rings, balls, wheels, or spheres. Said catalyst preferably comes in the form of extrudates of a size of between 1 and 10 mm.

Said second oligomerization stage e) of the process according to the invention advantageously operates at a temperature of between 100 and 300° C., at a pressure of between 2 and 6 MPa, and at an hourly speed by weight (mass rate of the feedstock per gram of catalyst) of between 0.1 and 5 $h^{-1}$. It is advantageously implemented in at least one reactor that operates in a fixed bed.

The effluent that is obtained from said second oligomerization stage is an olefinic effluent that comprises at least 50% by weight, relative to the total mass of olefins that are contained in said olefinic effluent, of olefins that have a number of carbon atoms that is greater than or equal to 8. Said olefinic effluent that is produced during said second oligomerization stage e) can also comprise, in a minority proportion, hydrocarbons that have at most 8 carbon atoms per molecule. In particular, it can comprise less than 50% by weight, and preferably less than 45% by weight, relative to the total mass of the olefins that are contained in said olefinic effluent, whereby olefinic hydrocarbons for the most part have a number of carbon atoms of between 4 and 8.

According to a first embodiment of said second oligomerization stage e), at least some, i.e., at least 50% by weight and preferably at least 85% by weight of the effluent that is obtained from said stage d), and very preferably all of the effluent that is obtained from said first oligomerization stage d), is introduced into at least one reactor that carries out the implementation of said second oligomerization stage e). In accordance with said first embodiment of said stage e), the effluent that is obtained from said first oligomerization stage d) advantageously is not subjected to any particular treatment, in particular at any separation stage, in such a way that all of the hydrocarbons that are present in said effluent that is obtained from said stage d), in particular olefins for the most part of C4-C8 and to a lesser extent of C9+, are present in the feedstock that is used for the implementation of said stage e).

According to a second embodiment of said second oligomerization stage e), the feedstock that is used for the implementation of said second oligomerization stage e) is obtained after the implementation of at least one separation stage that is carried out from the effluent that is obtained from said first oligomerization stage. In accordance with said second embodiment of said stage e), at least some, preferably all, C2-C4 olefinic hydrocarbons that are present in the effluent that is obtained from said first oligomerization stage and/or at least some, preferably all, C9+ olefinic hydrocarbons that are present in the effluent that is obtained from said first oligomerization stage are removed from said feedstock that is used for the implementation of said second oligomerization stage e). In a very preferred manner, at least some, and preferably all, C9+ olefinic hydrocarbons that are present in the effluent that is obtained from said first oligomerization stage are removed from said feedstock that is used for the implementation of said second oligomerization stage e).

In accordance with said second embodiment of said second oligomerization stage e), at least one separation stage is implemented between the first oligomerization stage d) and the second oligomerization stage e). Said separation stage(s) is (are) carried out in such a way as to produce different olefinic streams, of different chemical compositions, from said light olefinic effluent that is produced at the end of said first oligomerization stage d).

According to a first variant of said second embodiment of said second oligomerization stage e), said separation stage produces at least one olefinic hydrocarbon-containing effluent that has a number of carbon atoms that is for the most part greater than or equal to 4 (denoted C4+ olefinic effluent in the description below) and at least one light olefinic, hydrocarbon-containing effluent that has a number of carbon atoms that is for the most part between 2 and 4 (C2-C4 light olefinic effluent). Said C2-C4 light olefinic effluent is an effluent that advantageously comprises at least 50% by weight, preferably at least 60% by weight, and in a more preferred way at least 65% by weight, of olefinic compounds that have a number of carbon atoms of between 2 and 4 and can also advantageously comprise less than 50% by weight of olefinic compounds that have a number of carbon atoms that is greater than or equal to 5, whereby the percentages by weight are expressed relative to the total mass of said C2-C4 light olefinic effluent that is obtained from the separation stage. Said C2-C4 light olefinic effluent is advantageously recycled, in full, to the first oligomerization stage d). The olefinic, hydrocarbon-containing effluent that has a number of carbon atoms that is for the most part greater than or equal to 4 obtained from said separation stage (C4+ olefinic effluent) is an effluent that advantageously comprises at least 50% by weight, preferably at least 60% by weight, of olefinic hydrocarbons that have a number of carbon atoms that is between 4 and 8 and that comprises less than 50% by weight and preferably less than 40% by weight, of olefinic hydrocarbons that have a number of carbon atoms that is greater than or equal to 9, whereby the percentages by weight are expressed relative to the total mass of olefins that are present in the C4+ olefinic effluent that is obtained from said separation stage. Said olefinic hydrocarbon-containing effluent that has a number of carbon atoms that is for the most part greater than or equal to 4 that is obtained from said separation stage is used as a feedstock for the implementation of said second oligomerization stage.

According to a second variant of said second embodiment of said second oligomerization stage e), said olefinic, hydrocarbon-containing effluent that has a number of carbon atoms that is for the most part greater than or equal to 4, obtained from said separation stage that is implemented for the production of said first variant described above, is subjected to a second separation stage in such a way as to extract at least some, preferably all, olefinic hydrocarbons that have at least 9 carbon atoms. The result is the production of a C9+ olefinic effluent and a C4-C8 olefinic effluent from which at least some, preferably all, C9+ hydrocarbons are removed. Said C4-C8 olefinic effluent is used as a feedstock for the implementation of said second oligomerization stage. Said C9+ olefinic effluent is an effluent that advantageously comprises at least 50% by weight and preferably at least 70% by weight of olefinic compounds that have a number of carbon atoms that is greater than or equal to 9 and that also advantageously comprises less than 50% by weight and preferably less than 30% by weight of olefinic compounds that have a number of carbon atoms that is less than 9, whereby the percentages by weight are expressed relative to the total mass of the olefins that are present in the C4+ olefinic effluent that enters into said second separation stage. In an advantageous manner, at least some, preferably all, of said C9+ olefinic effluent is sent directly into said stage g) for alkylation of the process according to the invention, described below.

Said separation stage(s), advantageously implemented between the first oligomerization stage d) and the second oligomerization stage e) of the process of the invention, can be implemented by any method that is known to one skilled in the art. It (they) can be implemented, for example, by the combination of one or more high- and/or low-pressure and high- and/or low-temperature separator tanks and/or by the implementation of distillation stages that comprise one or more distillation column(s), or else by the use of molecular sieves or adsorbents whose purpose is the residual elimination of water.

In accordance with said stage f) of the process of the invention, said olefinic effluent that is obtained from said second oligomerization stage e) and that comprises at least 50% by weight, relative to the total mass of olefins contained in said olefinic effluent, of olefins that have a number of carbon atoms that is greater than or equal to 8, is subjected to at least one fractionation stage in such a way as to recover at least one olefin-enriched olefinic stream that has a number of carbon atoms that is greater than or equal to 9. Said olefinic stream advantageously comprises olefins that have 9 to 16 carbon atoms per molecule and in a very preferred manner 10 to 14 carbon atoms per molecule. In a preferred manner, said stream comprises at least 90% by weight of olefins that have a number of carbon atoms that is greater than or equal to 9, and in a very preferred manner, said stream consists entirely of olefins that have a number of carbon atoms that is greater than or equal to 9. The C9+ olefins, preferably the C9-C16 olefins, and very preferably the C10-C14 olefins, present in said stream, are called C9+ bio-olefins, preferably C9-C16 bio-olefins, and very preferably C10-C14 bio-olefins because they initially come from a bioethanol feedstock.

The fractionation stage according to said stage f) of the process according to the invention produces at least one olefin-enriched olefinic stream that has a number of carbon atoms that is greater than or equal to 9 (C9+ bio-olefins) and at least one olefin-enriched olefinic stream that has a number of carbon atoms that is between 4 and 8 (C4-C8 bio-olefins). At least one part of said C4-C8-bio-olefin-enriched stream is advantageously recycled to said second oligomerization stage e) of the process according to the invention and mixed with the feedstock of stage e). Said fractionation stage also advantageously leads to the production of a light effluent that comprises C2-C4 olefinic compounds, whereby said light effluent can also be separated to be upgraded in pure form or in a mixture. Some or all of said light effluent is advantageously recycled to said first oligomerization stage d) of the process according to the invention.

Said fractionation stage f) according to the process of the invention is implemented by any method that is known to one skilled in the art, for example by distillation.

In accordance with the process according to the invention, said C9+-bio-olefin-enriched stream, produced at the end of said fractionation stage f), is used as a feedstock for the implementation of said alkylation stage in accordance with said stage g), described later in this description. Said C9+ bio-olefins are branched olefins, i.e., they have at least one branching on the olefinic alkyl chain. The branching that is present on the olefinic alkyl chain of the C9+ bio-olefins is preferably a methyl group. The number of branches that are present on said olefinic alkyl chain is advantageously between 1 and 5 and is adjusted as a function of the composition of the catalyst that is used for the implementation of said second oligomerization stage e) of the process according to the invention. In particular, the use of a zeolitic catalyst in said stage e) promotes the production of C9+ bio-olefins having a number of branches of between 1 and 3. The number of branches is advantageously determined by NMR of the carbon.

In accordance with stage g) of the process according to the invention, said C9+-bio-olefin-enriched stream, produced at the end of said fractionation stage f), is introduced into at least one reactor that carries out the alkylation of said C9+ olefins, preferably C9-C16 olefins, and very preferably C10-C14 olefins, by at least one aromatic feedstock that comprises at least one compound that has a benzene core. Said C9+-bio-olefin-enriched stream, used as a feedstock for the implementation of said alkylation stage g), comprises at least 90% by weight of olefins that have a number of carbon atoms that is greater than or equal to 9, and in a very preferred manner, said stream consists entirely of olefins that have a number of carbon atoms that is greater than or equal to 9.

According to said alkylation stage g), said aromatic feedstock can come from any source that is known to one skilled in the art. In a preferred manner, said aromatic feedstock comprises benzene. Said aromatic feedstock that is used for the implementation of said stage g) is, for example, obtained from a fossil source, in particular petroleum or carbon. In an advantageous manner, it is obtained from a renewable source: in particular, said aromatic feedstock is advantageously obtained by transformation of bioethanol on a zeolitic acid catalyst or by transformation of glucose to produce aromatic compounds including benzene. The transformation of bioethanol into benzene on a zeolitic acid catalyst was already described by Madeira et al. (Applied Catalysis. A, 2009, Vol. 367, Nos. 1-2, 39-46). The zeolite ZSM-5 is particularly preferred in the composition of the zeolitic catalyst. The transformation of glucose into benzene was described by Carlson et al. (Journal of Catalysis, 270, 2010, 100-124).

Said alkylation stage g) is implemented in at least one reactor that operates either by homogeneous catalysis or by heterogeneous catalysis. For an implementation of said stage g) by homogeneous catalysis, said reactor is provided with at least one liquid acid catalyst, preferably hydrofluoric acid HF or sulfuric acid $H_2SO_4$. For an implementation of said stage g) by heterogeneous catalysis, said reactor is provided with at least one solid acid catalyst, in particular an amorphous acid catalyst, or a zeolitic acid catalyst. A preferred amorphous acid catalyst comprises at least one silica-alumina or a fluoridated silica-alumina. A preferred zeolitic acid catalyst comprises at least one zeolite that is selected from the group that consists of the zeolites of the following structural types: FAU, MOR, MTW, OFF, MAZ, BEA and EUO. Among the zeolites of the FAU structural type, the zeolite Y and the zeolite Y exchanged with rare earths (REY) are preferred. Among the zeolites of the MOR structural type, the zeolite mordenite is preferred. Among the zeolites of the MTW structural type, the zeolite ZSM-12 is preferred. Among the zeolites of the OFF structural type, the zeolite offretite is preferred. Among the zeolites of the MAZ structural type, the zeolite ZSM-4 is preferred. Among the zeolites of the BEA structural type, the zeolite beta is preferred, and among the zeolites of the EUO structural type, the zeolite EU-1 is preferred.

Said zeolitic acid catalyst advantageously comprises a mixture of zeolites of different structural types, for example a mixture of at least two zeolites of different structural types selected from among the zeolites of the following structural types: FAU, MOR, MTW, OFF, MAZ, BEA and EUO. It may involve in particular a mixture of zeolites that consists of at least one zeolite Y and at least one zeolite of the MOR structural type, preferably a mordenite. The zeolite(s) that is (are) present in the alkylation catalyst preferably comprise(s) at least one element X that is selected from among silicon and germanium, very preferably silicon, and at least one element T that is selected from among aluminum, iron, gallium and boron, very preferably aluminum, according to an overall atomic X/T ratio that is greater than or equal to 4. The zeolite(s) that is/are present in the alkylation catalyst generally come(s) in acid form in such a way that the content of alkaline element, in particular sodium, is such that the alkaline element/T atomic ratio is less than 0.5, preferably less than 0.1, and in a more preferred manner less than 0.02.

In a very preferred manner, said stage g) is implemented in the presence of at least one zeolitic catalyst, preferably in the presence of at least one catalyst that comprises at least one zeolite Y and very preferably a dealuminified zeolite Y.

Said alkylation catalyst advantageously comprises at least one oxide matrix, in particular alumina or silica. It comes in the form of seeds of different shapes and sizes. It is preferably used in the form of cylindrical or multilobar extrudates such as bilobar, trilobar, or multilobar extrudates of straight or twisted shape, but it can optionally be manufactured and used in the form of crushed powder, tablets, rings, balls, or disks. A preferred zeolitic catalyst contains 1 to 95% by weight, preferably 3 to 90% by weight, and more preferably 5 to 85% by weight of at least one zeolite that is selected from among the zeolites of the following structural types: FAU, MOR, MTW, OFF, MAZ, BEA and EUO, and at least one matrix that ensures the make-up to 100% by weight.

In the implementation by heterogeneous catalysis, said alkylation stage g) advantageously operates at a temperature of between 30 and 400° C., preferably between 50 and 350° C., and in a very preferred manner between 70 and 300° C., at a pressure of between 0.1 and 10 MPa, preferably between 1 and 7 MPa, and with an hourly volumetric flow rate of between 0.01 and 200 $h^{-1}$, preferably between 0.5 and 80 $h^{-1}$ (liquid hydrocarbon volume that corresponds to the olefinic stream and to the aromatic feedstock per volume of catalyst and per hour). The aromatic feedstock/olefinic stream molar ratio is between 2 and 50, preferably between 5 and 35. Said stage g) preferably uses at least one alkylation catalyst that operates in a fixed bed or in a moving bed. One preferred embodiment of said alkylation stage g), when said catalyst is a solid acid catalyst, consists in implementing at least two alkylation reactors in parallel in such a way as to allow the rejuvenation of the alkylation catalyst that is present in the reactor that does not operate in an operational mode. Such an implementation is described in particular in the patent application US 2009/062583.

In the implementation by homogeneous catalysis, said alkylation stage g) advantageously operates at a temperature of between 10 and 80° C., preferably between 20 and 60° C., and in a preferred manner between 30 and 50° C. The operating pressure is such that the reagents and the acid catalyst are in the liquid phase; thus, the pressure is advantageously between 0.2 and 4 MPa, preferably between 0.2 and 3 MPa. The acid/hydrocarbon-containing feedstock volumetric ratio is between 0.1 and 10, preferably between 1 and 3. The (compound(s) having a benzene core that is present in the aromatic feedstock)/bio-olefins molar ratio is generally between 1 and 15 and in a preferred way between 5 and 12. The contact time in the reactor is between 5 and 50 minutes and in a preferred way between 20 and 40 minutes.

Said alkylation stage g) leads to the production of at least one aromatic compound that belongs to the family of alkylbenzenes. More specifically, said compound(s) is (are) (one of the) aromatic compound(s) whose benzene core carries at least one saturated and branched alkyl chain, preferably a single branched saturated alkyl chain (monoalkylbenzenes), having at least 9 carbon atoms, preferably having between 9 and 16 carbon atoms, and in a more preferred manner, having between 10 and 14 carbon atoms. In an advantageous manner, said saturated alkyl chain carries 1 to 5 branches, and in a very advantageous manner, it carries 1 to 3 branches. In accordance with the invention, the aromatic compound(s) produced at the end of said alkylation stage g) does (do) not belong expressly therefore to the known family of the LAB designating the linear alkylbenzenes but to the family of the MAB designating the modified alkylbenzenes and more specifically the family of modified monoalkylbenzenes. The majority of the monoalkylbenzenes that are produced by the process of the invention are modified monoalkylbenzenes, i.e., at least 75% by weight, preferably at least 90% by weight, of the monoalkylbenzenes produced are monoalkylbenzenes whose alkyl chain is branched, preferably by a methyl group. In a very preferred manner, all of the monoalkylbenzenes produced by the process of the invention are modified monoalkylbenzenes.

According to a particular embodiment of the process according to the invention, the effluent that is obtained from said alkylation stage is fractionated in such a way as to collect separately at least one first fraction that contains said compound that is present in the aromatic feedstock, preferably benzene, at least one second fraction that contains at least said compound that belongs to the family of alkylbenzenes, preferably containing at least said compound(s) belonging to the family of modified monoalkylbenzenes, and at least one third fraction that contains at least one polyalkylbenzene, in particular at least one dialkylbenzene.

BRIEF DESCRIPTION OF THE DRAWINGS

Various features and attendant advantages of the present invention will be more fully appreciated as the same becomes better understood when considered in conjunction with the accompanying drawing, in which like reference characters designate the same or similar parts throughout the several views, and wherein:

Figure 1:
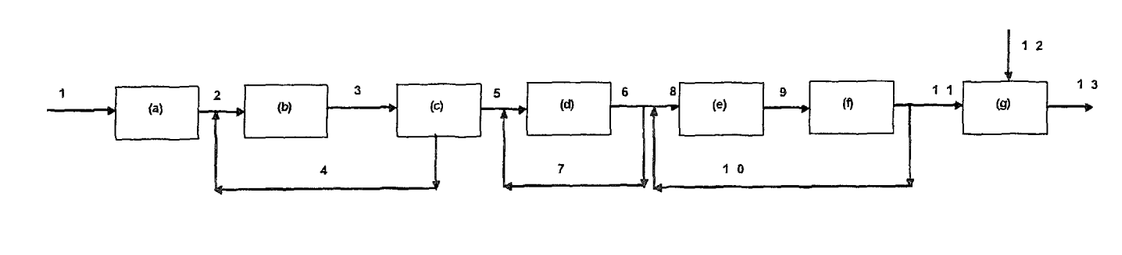

The invention will be better understood from reading the detailed example below, illustrating a particular embodiment of the process according to the invention and shown in FIG. 1.

A bioethanol feedstock is introduced into the purification stage a) via the pipe (1); the effluent that is obtained from stage a) via the pipe (2) then undergoes dehydration in accordance with stage b) of the process according to the invention. The ethylenic effluent (3) of stage b) is sent into a separation/purification stage c), whose aqueous effluent is recycled to stage b) of the process via the pipe (4). The effluent of stage c) that is for the most part ethylene (5) then undergoes a first oligomerization stage d) so as to produce a light olefinic effluent whose olefins have a number of carbon atoms of between 4 and 8. At the end of said first oligomerization stage, a separation, not shown in FIG. 1, is advantageously implemented on the pipe (6) by any method that is known to one skilled in the art, so as to allow an olefinic recycling (7) of olefinic compounds having a number of carbon atoms of between 2 and 4 upstream from stage d) so as to improve the production of the desired C4-C8 olefinic fraction at the output of stage d) and that constitutes the stream (8). Said C4-C8 olefinic fraction is subjected to a second oligomerization stage e) so as to produce an effluent (9) that contains for the most part olefinic compounds that have a number of carbon atoms that is greater than or equal to 8. At the end of this second oligomerization stage, a separation f) is implemented on the pipe (9) by any method that is known to one skilled in the art, so as to allow an olefinic recycling (10) of compounds that have a number of carbon atoms of between 4 and 8 upstream from stage e). Said separation stage f) makes it possible to collect an olefinic stream (11) that is enriched with C9+ bio-olefins that is introduced into an alkylation zone g) in the presence of an aromatic feedstock (12) that comprises benzene. The effluent (13) that is produced at the end of said alkylation zone comprises the desired modified monoalkylbenzenes that are collected separately in a fraction that is obtained after the implementation of a fractionation stage, not shown in FIG. 1, of the effluent (13).

EXAMPLE

The bioethanol feedstock that is used is a bioethanol feedstock that has been treated and purified by a series of stages of distillation and being run over molecular sieves so as to meet the following specifications and whose composition is provided in Table 1:

TABLE 1

| Composition of the Purified Bioethanol Feedstock | |
|---|---|
| Composition | Content in % by Weight |
| EtOH | 99% |
| Methanol | <0.05% |
| Butanol | <0.1% |
| Other Alcohols | <0.05% |
| Total Content of Alcohol Other than Ethanol | <0.2% |
| Oxidized Compounds Other than Alcohols | <0.1% |
| $H_2O$ | <1% |
| Cationic Impurities (Total Content) | <0.005% |
| Anionic Impurities (Total Content) | <0.005% |

The purified bioethanol feedstock then undergoes a dehydration stage, carried out in the presence of a C1 zeolitic catalyst, for producing an effluent that is for the most part ethylene, comprising water.

Preparation of the C1-Catalyst that is Used in Stage b) of the Process According to the Invention The dehydration catalyst of stage b) is prepared according to the teaching that is described in the patent application US 2009/088595. Said C1 catalyst is a zeolitic catalyst (ZSM-5) that comprises an alumina-based substrate; it comes in the form of spherical balls. Said C1 catalyst is prepared as follows:

An emulsion is prepared by introducing 244 g of water, 49 g of pore-forming agent that consists of Isane® (marketed composition that comprises several aromatic components) and 2.9 g of surfactant that consists of Galoryl® (non-ionic emulsifying agent that is marketed by the Comptoir Français des Produits Industriels) into a one-liter beaker. The mixture is put on stir at 500 rpm for 15 minutes.

A suspension is prepared by introducing 2,198 g of permuted water and 69 g of nitric acid at 59.68% by weight into a 4-liter beaker, whereby the mixture is stirred at 400 rpm for 5 minutes. 450 g of PURAL SB3 (fire loss=26.10%, pseudo-boehmite marketed by SASOL) is then added, and the mixture (permuted water, nitric acid, and PURAL SB3) is stirred at 1600 rpm for 14 minutes. 332 g of zeolite ZSM-5 in H form or an Si/Al ratio equal to 140, marketed by the Zeolyst Company, is then added to the mixture (permuted water, nitric acid, and PURAL SB3), the resulting mixture is stirred at 1600 rpm for 3 minutes, and then the emulsion that is formed by water, isane and galoryl is added to said mixture. The combination is stirred under 1600 rpm for 13 minutes, and then the stirring speed is reduced to 625 rpm for 70 minutes.

The viscosity of said mixture is then measured by means of a plane-plane rheometer for a shear speed gradient of 100 s$^{-1}$ and is equal to 270 mPa·s.

The shaping is done by drop coagulation by using a 9.4-liter glass column. Said column is charged with 7 liters of an ammonia solution that has a concentration equal to 28 g/l, 0.4 liter of an ammonyl solution (alkyl dimethyl benzyl ammonium bromide in aqueous solution, marketed by the SEPIC SA Company) with 1% by mass and 0.7 liter of isane. The column is topped by a draining pot that consists of nozzles, each one being equipped with a circular opening that has a diameter that is equal to 1 mm. The suspension is introduced into said draining pot, whereby the draining rate is such that 80 droplets are drained per minute and per nozzle. The droplets then fall into the isane phase and then into the ammonia phase at 28 g/l, with the isane phase—ammonia phase interface consisting of ammonyl. The thus obtained balls are placed in a ventilated box at ambient temperature for one night to carry out a first mild drying and then are placed in an oven for one night at 100° C. The dried balls are calcined for 2 hours in a muffle furnace at 600° C. The catalyst C1 that has the following textural and mechanical characteristics is thus obtained: a BET surface area that is equal to 321 m$^2$/g, a pore volume that is measured by mercury porosimetry that is equal to 0.41 ml/g, a macropore volume that is measured by mercury porosimetry that is equal to 0.12 ml/g, a mesopore volume that is measured by mercury porosimetry that is equal to 0.29 ml/g, and a ball size of between 1.8 and 2.2 mm. The C1 catalyst has a mechanical strength such that the grain-to-grain crushing (EGG) is equal to 26 N.

The dehydration stage b) is implemented in such a way as to maximize the ethylene production: it operates in the presence of the C1 zeolitic catalyst, prepared according to the protocol described above, and at a temperature of 400° C., at a pressure of 0.1 MPa, and at an hourly speed by weight of 5 h$^{-1}$. Said stage b) is implemented in a fixed bed.

The dehydration stage b) produces a hydrocarbon-containing effluent that is for the most part ethylene, comprising water. The distribution by weight of the different components of said effluent that is obtained from the dehydration stage is provided in Table 2.

TABLE 2

Distribution of the Effluent that is Produced During Stage b)

| Distribution | % by Weight Relative to the Mass of the Effluent Produced |
|---|---|
| Water | 39.5% by Weight |
| Hydrocarbon-Containing Effluent | 60% by Weight |
| Ethanol | 0.5% |

The composition of the hydrocarbon-containing effluent that is for the most part ethylene and that is produced during the dehydration stage b) is measured by gas phase chromatography (CPG) and provided in Table 3.

TABLE 3

Composition of the Effluent that is for the Most Part Ethylene Formed During the Dehydration of Ethanol (Stage b)

| Components | Proportion by Weight (% by Weight) Relative to the Total Mass of the Hydrocarbon-Containing Compounds Formed |
|---|---|
| Ethylene | 98.5 |
| Hydrocarbons that Have More than 3 Carbon Atoms | 1.5 |
| Oxidized Compounds | <0.1 |

The conversion of the ethanol in stage b) is 99.5%. Starting from 1 kg/h of purified bioethanol, 591 g/h of ethylene is obtained.

Stage c): Separation of Water.

The effluent that is for the most part ethylene obtained from stage b) then undergoes a series for separation and purification by being run over a column for washing with water, and then in a column for absorption with methyldiethylamine and then by being run over a column for washing with soda and in drying agents in such a way as to remove some of the water formed during stage b) from said effluent that is for the most part ethylene. The effluent that is obtained from said stage c) comprises 100 ppm of water.

Stage d): First Oligomerization Stage (Implementation by Heterogeneous Catalysis).

The ethylene effluent obtained from separation stage c) is then sent into a first oligomerization reaction unit that operates in the presence of a supported catalyst C3, whose preparation is described below, at a temperature of 140° C., at a pressure of 3.0 MPa, and at an hourly speed by weight of 1.0 h$^{-1}$. Said catalyst C3 has a composition Ni/SiO$_2$—AlO$_3$ and is prepared according to the protocol described below.

Preparation of the Catalyst C3 Used in Stage d) Implemented by Heterogeneous Catalysis.

The substrate of the catalyst is prepared as follows: an aluminum hydroxide powder is mixed with a silica sol that is prepared by decationizing resin exchange, and then it is filtered on resin with porosity 2. The concentrations of silica sol and aluminum hydroxide powder are adjusted in such a way as to obtain a final composition of 80% by weight of Al$_2$O$_3$ and 20% by weight of SiO$_2$. The shaping is done in the presence of 15% by weight of nitric acid relative to the anhydrous product. The mixed paste is then extruded through a die with a 1.4 mm diameter. The extrudates SA1 that are thus obtained are dried at 120° C. and then calcined at 550° C.

40 g of silica-alumina SA1 in the form of extrudates is impregnated in the dry state with a solution that contains 6.5 g of hexahydrate nickel nitrate. The solid that is obtained is dried in air at 150° C. for 2 hours and then calcined at 500° C. for 3 hours. The catalyst C3 that is thus obtained has 3.2% by weight of nickel relative to the total mass of catalyst.

The composition of the light olefinic effluent, produced during said first oligomerization stage, is provided in Table 4.

TABLE 4

Composition of the Light Olefinic Effluent Obtained from the First Oligomerization Stage d)

| | % by Weight Relative to the Total Mass of the Olefins Contained in the Effluent that is Produced |
|---|---|
| Ethylene | 5 |
| C4+ Olefins | 95% |
| | Including 73.7% by Weight of C4-C8 |
| | 26.3% by Weight of C9+ |

At the end of this stage, starting from 1 kg/h of purified bioethanol introduced into stage b), 561 g/h of olefins that have 4 or more carbon atoms is obtained.

The effluent that is obtained from the first oligomerization stage d) is sent to the second oligomerization stage e).

Stage e): Second Oligomerization Stage

The second oligomerization stage operates in the presence of a zeolitic catalyst based on a zeolite ZSM-5 at a temperature of 220° C., at a pressure of 4.0 MPa, and at an hourly speed by weight of 0.7 h$^{-1}$. Said zeolitic catalyst contains a commercial zeolite ZSM-5 that has a content by weight of sodium of 0.05% and an Si/Al atomic ratio that is equal to 40. The zeolite is shaped by extrusion with alumina in such a way that the oligomerization catalyst is formed by 50% by weight of zeolite ZSM-5 and 50% by weight of alumina. Next, the extrudates are dried and then calcined at 550° C.

The composition of the effluent that is obtained from the second oligomerization stage is described in Table 5.

TABLE 5

Composition of the Olefinic Effluent Obtained from the
Second Oligomerization Stage e)

|  | % by Weight Relative to the Total Mass of the Olefins Contained in the Exiting Effluent |
|---|---|
| Ethylene | 5 |
| Propylene | 1 |
| C4-C8 Olefins | 23.5 |
| C8+ Olefins | 70.5 |

The olefinic effluent that is obtained from the second oligomerization stage e) then undergoes a fractionation stage f), by distillation, in such a way as to collect a light effluent that comprises the C2-C4 compounds, a fraction formed by C4-C9 bio-olefins, a fraction formed by C10-C14 bio-olefins, and a C15+ heavy fraction. The yields of the different fractions are indicated in Table 6.

TABLE 6

Yields of Fractions Obtained at the End of the Stage of the
Second Oligomerization Stage

| Hydrocarbon-Containing Fractions | % by Weight |
|---|---|
| C2-C4 | 12.0% |
| C4-C9 Bio-olefins | 17% |
| C10-C14 Bio-olefins | 62.6% |
| C15+ | 8.4% |

At the end of this stage, starting from 1 kg/h of purified bioethanol introduced in stage b), 370 g/h of an olefinic fraction formed by C10-C14 bio-olefins is obtained. Said fraction that is formed by C10-C14 bio-olefins is used as a feedstock for the implementation of the alkylation stage. An NMR analysis of the carbon reveals the presence of two branches on the olefinic chain of the C10-C14 bio-olefins.

Stage g): Alkylation Stage

The reaction for alkylation of benzene in the presence of the olefinic feedstock formed from C10-C14 bio-olefins is carried out in a catalytic reactor that comprises only a single reaction zone that contains 50 cm$^3$ of a zeolitic catalyst in the form of extrudates. The alkylation catalyst contains a commercial zeolite USY that has a content by weight of sodium of 0.14% and an Si/Al atomic ratio that is equal to 38. The zeolite is shaped by extrusion with the alumina in such a way that the alkylation catalyst is formed by 50% by weight of zeolite USY and 50% by weight of alumina. Next, the extrudates are dried, and then calcined at 550° C.

The operating conditions for the alkylation of benzene by the C10-C14 bio-olefins are as follows:

Temperature: 135° C.

Pressure: 4 MPa

VVH=1 h$^{-1}$ (cm$^3$ of benzene feedstock+C10-C14 bio-olefins per cm$^3$ of catalyst and per hour)

Molar ratio of benzene/C10-C14 bio-olefins: 30

A feedstock is prepared that contains a mixture of benzene and the C10-C14 bio-olefinic fraction that is obtained at the end of stage f). This feedstock is introduced at the input of the catalytic reactor where the alkylation reaction takes place.

The results that are obtained are presented in Table 7. They are expressed in terms of stability of the catalyst and the selectivity with regard to the modified alkylbenzenes.

TABLE 7

Results at the End of the Implementation of the Alkylation Stage

| Cycle Time with Conversion of C10-C14 Bio-olefins >95% | >500 Hours |
|---|---|
| MAB Selectivity | 95% |

The MAB selectivity is defined as being equal to the mass ratio [MAB/(MAB+LAB)], with the LAB being the linear alkylbenzenes and the MAB being the modified alkylbenzenes.

The results that appear in Table 7 demonstrate an optimal stability of the alkylation catalyst over a long period. The process according to the invention leads to the vast majority of the production of modified monoalkylbenzenes.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding FR application Ser. No. 10/01,950, filed May 6, 2010 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. Process for the production of at least one aromatic compound that belongs to the family of alkylbenzenes in the presence of at least one aromatic feedstock that comprises at least one compound that has a benzene core and at least one olefinic stream that is produced from an ethanol feedstock, itself produced from a renewable source that is obtained from the biomass, whereby said process comprises at least:
   a) A stage for purification of said ethanol feedstock,
   b) A stage for dehydration of said purified ethanol feedstock, obtained from said stage a), into an effluent that is for the most part ethylene, comprising water, whereby said stage operates in the presence of at least one amorphous acid catalyst or at least one zeolitic acid catalyst,
   c) At least one stage for separation of the water that is present in said effluent that is for the most part ethylene obtained from said stage b),
   d) A first stage for oligomerization of said effluent that is for the most part ethylene, obtained from said stage c), in the presence of at least one catalyst that comprises at least one element of group VIII for producing at least one light olefinic effluent that comprises at least 50% by weight, relative to the total mass of the olefins that are contained in said light olefinic effluent, of olefins that have a number of carbon atoms that is greater than or equal to 4,
   e) A second stage for oligomerization of at least some of the effluent that is obtained from said stage d) in the presence of at least one amorphous catalyst or at least one zeolitic catalyst for producing at least one olefinic effluent that comprises at least 50% by weight, relative to the total mass of the olefins that are contained in said olefinic effluent, of olefins that have a number of carbon atoms that is greater than or equal to 8, f) At least one stage for fractionation of the effluent that is obtained from said oligomerization stage e) in such a way as to recover at least one olefin-enriched olefinic stream that has a number of carbon atoms that is greater than or equal to 9, g) An alkylation stage of said olefinic stream that is obtained from said stage f) by at least one aromatic feedstock that comprises at least one compound that has a benzene core.

2. Process for production according to claim 1, such that said dehydration stage b) operates in the presence of a zeolitic acid catalyst that comprises at least one zeolite that has a structural type that is selected from among the following structural types: MFI, FAU, MOR, FER and BEA.

3. Process for production according to claim 1, such that said effluent that is for the most part ethylene produced by said stage b) comprises at least 95% by weight of ethylene relative to the total mass of the carbon-containing compounds that are formed and present in said effluent.

4. Process for production according to claim 1, such that said dehydration stage is implemented in at least one reactor that operates in a fixed bed, a moving bed, or a fluidized bed.

5. Process for production according to claim 1, such that said separation stage is followed by at least one stage for purification of said effluent that is for the most part ethylene from which water was eliminated in advance.

6. Process for production according to claim 1, such that the content of water that is present in the effluent, obtained from said stage c) and sent into said first oligomerization stage d), is between 0 and 1,000 ppm.

7. Process for production according to claim 1, such that among the olefins that have a number of carbon atoms that is greater than or equal to 4 and that are present in said light olefinic effluent obtained from said stage d), the C4-C8 olefins are in the majority relative to the C9+ olefins.

8. Process for production according to claim 1, such that said first oligomerization stage is implemented by heterogeneous catalysis in the presence of at least one catalyst that comprises at least one element of group VIII and at least one porous oxide refractory substrate.

9. Process for production according to claim 1, such that said first oligomerization stage is implemented by homogeneous catalysis in the presence of at least one homogeneous catalyst that contains at least one metal precursor that comprises at least one metal of group VIII that is selected from among nickel and iron.

10. Process for production according to claim 1, such that at least one separation stage is implemented between the first oligomerization stage d) and the second oligomerization stage e).

11. Process for production according to claim 1, such that said olefinic stream that is obtained at the end of said stage f) comprises olefins that have 10 to 14 carbon atoms per molecule.

12. Process for production according to claim 1, such that said olefinic stream that is obtained at the end of said stage f) comprises at least 90% by weight of olefins that have a number of carbon atoms that is greater than or equal to 9.

13. Process for production according to claim 1, such that said alkylation stage g) is implemented in at least one reactor that operates either by homogeneous catalysis or by heterogeneous catalysis.

14. Process for production according to claim 1, such that said aromatic compound that belongs to the family of alkylbenzenes is an aromatic compound whose benzene core carries at least one saturated and branched alkyl chain that has at least 9 carbon atoms.

15. Process for production according to claim 14, such that said saturated alkyl chain carries 1 to 5 branches.

* * * * *